United States Patent [19]

Cyronak et al.

[11] 4,426,403
[45] Jan. 17, 1984

[54] FLAVORING WITH ETHYL-2-METHYLTHIOISOBUTYRATE

[75] Inventors: Matthew J. Cyronak, Hightstown, N.J.; Paul R. Zanno, Hopewell Junction; Robert J. Soukup, New City, both of N.Y.

[73] Assignee: General Foods Corporation, White Plains, N.Y.

[21] Appl. No.: 360,857

[22] Filed: Mar. 22, 1982

[51] Int. Cl.$^3$ ............................................. A23L 1/226
[52] U.S. Cl. ..................................... 426/535; 560/152
[58] Field of Search ......................... 426/535; 560/152

[56] References Cited

U.S. PATENT DOCUMENTS 3,904,556 9/1975 Pettet et al. ...................... 560/152 X
4,332,829 6/1982 van den Bosch et al. .......... 426/535

OTHER PUBLICATIONS

Furia et al, Fenaroli's Handbook of Flavor Ingredients, 2nd Ed., vol. 2, 1975, CRC Press: Cleveland, pp. 183, 578, 579.

*Primary Examiner*—Joseph M. Golian
*Attorney, Agent, or Firm*—Thomas A. Marcoux; Joseph T. Harcarik; Daniel J. Donovan

[57] ABSTRACT

This invention relates to a foodstuff which contains an amount of an ethyl-methylthio substituted alkyl ester having the following structure:

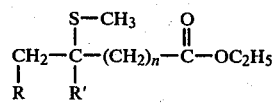

wherein R and R' independently is either hydrogen or an alkyl group of from one to three carbon atoms and n is either zero or one.

The ethyl-methylthio substituted alkyl ester will augment or enhance a fruity, vegetable or green pine needle flavor to the foodstuff.

3 Claims, No Drawings

FLAVORING WITH ETHYL-2-METHYLTHIOISOBUTYRATE

BACKGROUND OF THE INVENTION

1. Field of the Invention

This invention pertains to a foodstuff and, more particularly, to a foodstuff having an effective amount of a fruity, vegetable, or green pine needle flavorant.

2. Description of the Prior Art

Flavor is an important factor in food acceptance. With the increasing use of prepared foodstuffs there is expanded search for suitable new flavorants which augment or enhance flavor.

U.S. Pat. No. 3,870,800 to Pittett et al. states it relates to novel methods of altering the organoleptic properties of consumable materials such as foods and the like, and to compositions for effecting such methods and processing for the production of a number of derivatives of (methylthio) butane. U.S. Pat. No. 3,895,640 also to Pittet et al. states it relates to methods of altering the organoleptic properties of tobacco and tobacco substitutes and to composition for effecting such methods, such constituting a number of derivatives of (methylthio) butane. U.S. Pat. No. 3,904,556 again to Pittet et al. states it relates to novel methods of altering the organoleptic properties of consumable materials such as foods and the like, and to compostions for effecting such methods and processes for the production of a number of derivatives of (methylthio) butane. These patents state in Examples XVII that ethyl 4-(methylthio) butyrate is added to a cheese sauce to increase the notes usually present in surface-ripened cheese and to increase the cheese flavor intensity. In Examples XX this compound is added to tobacco to enhance the pineapple character of a fruit flavor for a tobacco. In Examples XXI this compound is added to a perfume formulation to impart a fruity ylang jasmin note to a floral essential oil composition.

SUMMARY OF THE INVENTION

This invention relates to a foodstuff comprising an amount of compound having the following structure:

$$\begin{array}{c} \text{S--CH}_3 \quad\quad \text{O} \\ | \quad\quad\quad\quad || \\ \text{CH}_2\text{--C--(CH}_2)_n\text{--C--OC}_2\text{H}_5 \\ | \quad\quad | \\ \text{R} \quad\quad \text{R}' \end{array}$$

wherein R and R' independently is either hydrogen or an alkyl group of from one to three carbon atoms and n is either zero or one.

It has been found when this invention is employed it enhances the fruity or vegetable flavor of foodstuff or augments a green pine needle or fruity flavor to foodstuff.

DESCRIPTION OF THE PREFERRED EMBODIMENT

This invention is directed to foodstuff having an amount of compound of the following structure:

$$\begin{array}{c} \text{S--CH}_3 \quad\quad \text{O} \\ | \quad\quad\quad\quad || \\ \text{CH}_2\text{--C--(CH}_2)_n\text{--C--OC}_2\text{H}_5 \\ | \quad\quad | \\ \text{R} \quad\quad \text{R}' \end{array}$$

wherein R and R' independently is either hydrogen or an alkyl group of from one to three carbon atoms and n is either zero or one.

These compounds augment or enhance the flavors of the foodstuff.

As used herein in regard to flavors, the term "augment" means supplying or imparting flavor character or note to otherwise bland, relatively tasteless substances or augmenting the existing flavor characteristic where a natural or synthetic flavor is deficient in some regard or supplementing the existing flavor impression to modify its quality, character or taste.

As used herein in regard to food flavors, the term "enhance" is used herein to mean the intensification of a flavor or aroma characteristic or note without the modification of the quality thereof. Thus, "enhancement" of a flavor or aroma means that the enhancement agent does not add any additional flavor note.

As used herein the term "foodstuff" includes both solids and liquids, and ingestible materials or chewable but noningestible materials such as chewing gum. Such materials usually do, but need not, have nutritional value. Thus, foodstuffs include soups, convenience foods, beverages, gelatin desserts, dairy products, candies, vegetables, cereals, soft drinks, snacks and the like.

Generally the flavors of the these compounds are fruity such as, but not limited to, pineapple, strawberry and berry. When n=0, R is hydrogen and R' is methyl e.g. the compound is ethyl 2-methylthio-isobutyrate the flavor in addition to fruity is pine needle.

The level at which the flavoring compound is effective in foodstuffs is generally within the range of from 0.004 to 20 parts per million and preferably from 0.04 to 10 parts per million of the foodstuff on an as-consumed basis.

The compounds of the present invention may be prepared from corresponding bromo acids by reaction with NaSCH to form the methylthio acids and then esterification in ethanol to yield the compound.

EXAMPLE 1

Ethyl 2-methylthioisobutyrate was synthesized according to the following procedure:

In a 2000 ml round bottom flask is added 1000 ml of absolute alcohol. To this is added 27.5 gms of sodium metal, the addition taking place in 3 portions with stirring. The mixture is cooled to 0° C. and 24 ml of methyl mercaptan is added. This solution is stirred for 1 hour at 0° C. and then 100 gms of α-Bromo Isobutyric acid is added. The mixture is then refluxed for 2 hours. After reacting, the mixture is poured into 600 ml of water, acidified to pH 3 with HCl and extracted with ether. The ether layer is washed with saturated NaCl, dried over sodium sulfate and concentrated.

The residue is taken up in 2000 ml or absolute ethanol to which is added 25 ml of BF$_3$ etherate. This mixture is refluxed for 2 hours and then partitioned between 400 ml of water and 300 ml of ether. The ether layer is separated and washed with saturated NaHCO$_3$, saturated NaCl, dried over NaSO$_4$ and concentrated. The residue was distilled under reduced pressure giving 24 gms of ethyl 2-methylthiosobutyrate. The compound had a green pine needle/berry flavor characteristic.

The obtained ethyl 2-methylthioisobutyrate was added at a level of 0.045 ppm to a strawberry flavored gelatin dessert. This dessert product had a better flavor which was best described as having a more green-fresh strawberry type impact than the control strawberry flavored gelatin dessert which did not incorporate any ethyl 2-methylthioisobutyrate.

EXAMPLE 2

Additional flavor compounds were synthesized in a similar fashion from the corresponding bromo or chloro substituted acids obtaining compounds with the following flavor characteristics:

| Compound | Flavor Character |
| --- | --- |
| Ethyl 3-methylthiobutyrate | pineapple/strawberry |
| Ethyl 4-methyl-3-methylthiobutyrate | pineapple |
| Ethyl 3-methyl-3-methylthiobutyrate | fruity/pineapple |
| Ethyl 2-methylthiobutyrate | carrot-top |

We claim:

1. A foodstuff comprising an amount of ethyl-2-methylthioisobutyrate of from about 0.004 to about 20 parts per million of the foodstuff on an as-consumed basis, said amount being effective to enhance or augment a green pine needle flavor in the foodstuff.

2. A foodstuff according to claim 1 wherein the amount is from about 0.04 to about 10 parts per million of the foodstuff on an as-consumed basis.

3. A foodstuff according to claim 1 wherein the foodstuff is a gelatin dessert.

* * * * *